| United States Patent [19] | [11] Patent Number: 4,826,917 |
|---|---|
| Kondo et al. | [45] Date of Patent: May 2, 1989 |

[54] METHOD OF PRODUCING HIGHLY ABSORBENT RESINS

[75] Inventors: Susumu Kondo, Kyoto; Tetsuo Moriya, Hirakata, both of Japan

[73] Assignee: Nippon Gohsei Kagaku Kogyo Kabushiki Kaisha, Osaka, Japan

[21] Appl. No.: 46,332

[22] Filed: May 6, 1987

[30] Foreign Application Priority Data

May 19, 1986 [JP] Japan ................... 61-115001

[51] Int. Cl.$^4$ ............................................. C08F 8/00
[52] U.S. Cl. ..................................... 525/59; 524/459
[58] Field of Search ........................... 524/459; 525/59

[56] References Cited

U.S. PATENT DOCUMENTS 3,586,689  6/1971  Nicherson et al. ................. 524/459
3,966,679  6/1976  Gross .............................. 260/47 EA
4,296,017  10/1981 Weissgerber et al. ............... 525/59
4,320,040  3/1982  Fujita et al. ..................... 524/459
4,351,922  9/1982  Yoshida et al. .................... 525/116
4,541,871  9/1985  Obayashi et al. ................... 106/197
4,666,975  5/1987  Yamasaki et al. ................... 524/733

*Primary Examiner*—C. Warren Ivy
*Assistant Examiner*—Alex H. Walker
*Attorney, Agent, or Firm*—Armstrong, Nikaido, Marmelstein, Kubovcik & Murray

[57] ABSTRACT

Polymerization of acrylic or methacrylic acid and a water-soluble acrylic or methacrylic acid salt in the presence of a carboxyl group-containing polyvinyl alcohol resin gives highly water-absorbing resins with the water absorbency, water absorption rate, water insolubility and other characteristics well balanced therein.

10 Claims, No Drawings

METHOD OF PRODUCING HIGHLY ABSORBENT RESINS

BACKGROUND OF THE INVENTION

This invention relates to a method of producing partially neutralized (meth)acrylic acid polymers excellent in water absorbing capacity.

Recently, water-absorbing resins are used very widely, for example in the field of hygiene (in sanitary napkins, tampons, diapers, disposable dusters, etc.), in the field of agriculture/horticulture (as water retaining agents), and in other fields (for coagulation of mud and sludge, prevention of dew condensation on building materials, dehydration of oils, etc.). Known water-absorbing resins include, among others, partially polybasic acid-crosslinked carboxymethyl cellulose, partially crosslinked polyethylene oxide, hydrolyzed starch-acrylonitrile graft polymers and partially crosslinked polyacrylic acid salts.

Among such resins, hydrolyzed starch-acrylonitrile graft polymers and partially crosslinked polyacrylic acid salts are particularly of practical use since they have relatively high water absorbing capacity.

Other noteworthy known ones are highly water-absorbing resins obtained by reversed-phase suspension polymerization of partially neutralized (meth)acrylic acid, namely a mixture of (meth)acrylic acid and a (meth)acrylic acid salt, if necessary in the presence of a protective colloid such as sorbitan fatty acid ester, cellulose ether, cellulose ester, polyvinyl alcohol or polyethylene oxide (cf. Japanese Kokai Tokkyo Koho Nos. 44627/1982, 62665/1984 and 186506/1985).

The term "reversed-phase suspension polymerization" as used herein means the polymerization of a monomer in the form of an aqueous solution suspended in a non-aqueous solvent.

Meanwhile, it is not the only requirement for highly water-absorbing resins that they should have a high degree of absorbency for water. It is also important that they should show a sufficiently high rate of water absorption upon coming into contact with water, namely a capacity for absorbing a sufficient quantity of water at a sufficient rate to render them of practical value, and at the same time have the so-called insolubility, namely the property of being insoluble when brought into contact with water.

However, none of the known absorbent resins has the above performance characteristics in a well-balanced manner. Solution of such problem will necessarily lead to an increase in the range of use of highly absorbent resins, hence is very much desired.

SUMMARY OF THE INVENTION

As a result of their intensive investigations, the present inventors found that when (meth)acrylic acid and a water-soluble (meth)acrylic acid salt are polymerized in the presence of a carboxyl group-containing polyvinyl alcohol resin, the product resin has all the required characteristics relative to the absorbency for water, rate of water absorption and insolubility in water in a well-balanced manner. In this respect, said resin is distinguished from the hitherto known absorbent resins. The present invention has been completed based on this finding.

DETAILED DESCRIPTION OF THE INVENTION

Typical examples of the carboxyl group-containing polyvinyl alcohol resin to be used in accordance with the invention are as follows:

(1) Saponified vinyl ester (vinyl acetate, vinyl formate, vinyl propionate, etc.)-ethylenically unsaturated carboxylic acid copolymers.

As the ethylenically unsaturated carboxylic acid, there may be mentioned such monocarboxylic acids as acrylic acid, methacrylic acid and crotonic acid and such dicarboxylic acids as maleic acid, maleic anhydride, fumaric acid, itaconic acid and itaconic anhydride. Salts of these carboxylic acids, such as sodium salt, monoesters thereof, such as monomethyl, monoethyl, monopropyl and monobutyl esters, and diesters thereof are also usable. In the case of diesters, however, it is necessary to select saponification conditions for the copolymer of said diester and vinyl acetate such that not only the vinyl acetate unit but also at least one ester group of said diester can be saponified.

Furthermore, saponified copolymers of a vinyl ester, an ethylenically unsaturated carboxylic acid and another copolymerizable monomer may also be used. As said monomer, there may be mentioned olefins such as ethylene, propylene, isobutylene, α-octene, α-dodecene and α-octadecene, long-chain or branched-chain alkyl vinyl esters such as vinyl versatate, nitriles such as acrylonitrile and methacrylonitrile, amides as acrylamide and methacrylamide, olefin-sulfonic acid such as etylenesulfonic acid, allylsulfonic acid and methallylsulfonic acid and salts of these, alkyl vinyl ethers, polyoxyalkylene allyl ethers, alkyl allyl ethers, saturated carboxylic acid allyl esters, vinyl ketones, N-vinylpyrrolidone, vinyl chloride, vinylidene chloride, acetoacetyl group-containing ethylenically unsaturated monomers, and oxyalkylene group-containing unsaturated monomers.

(2) Polyvinyl alcohol and derivatives thereof as post-modified for carboxyl group introduction.

Thus, esterification with a polybasic acid such as maleic acid or anhydride thereof, carboxyalkylation with a haloalkanecarboxylic acid such as monochloroacetic acid, and acetalization with a carboxyl group-containing aldehyde such as glyoxylic acid, among others, are performed.

(3) Polymers derived from polyvinyl alcohol or a derivative thereof by graft polymerization thereon of an ethylenically unsaturated carboxylic acid mentioned above under (1), such as acrylic acid, methacrylic acid, maleic acid, maleic anhydride, itaconic acid, itaconic anhydride and fumaric acid, or a salt or monoalkyl ester thereof.

The polyvinyl alcohol derivatives mentioned above under (2) and (3) include, among others, carbonyl group-containing polyvinyl alcohol, formalized, acetoacetalized, butyralized or urethanized polyvinyl alcohol, polyvinyl alcohol esterified with a sulfonic or carboxylic acid or the like, and cationized polyvinyl alcohol and, furthermore, saponified copolymers of a vinyl ester and a monomer copolymerizable therewith. Said monomer includes, among others, olefins such as ethylene, propylene, isobutylene, α-octene, α-dodecene and α-octadecene, long-chain alkyl vinyl esters such as vinyl versatate, unsaturated acids such as acrylic acid, methacrylic acid, crotonic acid, maleic anhydride and itaconic acid, salts and monoand dialkyl esters of such acids, nitriles such as acrylonitrile and methacrylonitrile, amides such as acrylamide and methacrylamide, olefin-sulfonic acids such as ethylenesulfonic acid, allylsulfonic acid and methallylsulfonic acid, salts of such sulfonic acids, alkyl vinyl ethers, polyoxyalkylene allyl ethers, alkyl allyl ethers, saturated carboxylic acid allyl esters, vinyl ketones, N-vinylpyrrolidone, vinyl chloride, vinylidene chloride, acetoacetyl group-containing ethylenically unsaturated monomers, and oxyalkylene group-containing unsaturated monomers.

It is desirable from the practical viewpoint that the carboxyl group content in said carboxyl group-containing polyvinyl alcohol resin should be 0.1–30 mole percent, preferably 0.5–10 mole percent, that the viscosity (at 20° C.) of a 4% aqueous solution of said resin should be 10–50 cps, preferably 20–30 cps, and that the degree of saponification should be within the range of 60–100 mole percent. When the carboxyl group content is below 0.1 mole percent, the water-soluble portion becomes large. When, conversely, said content exceeds 30 mole percent, the absorbency for water and the rate of water absorption become reduced.

In accordance with the invention, (meth)acrylic acid and a water-soluble (meth)acrylic acid salt are polymerized in the presence of the above carboxyl group-containing polyvinyl alcohol resin.

The term "(meth)acrylic acid and a water-soluble (meth)acrylic acid salt" as used herein means a mixture of (meth)acrylic acid and a water-soluble (meth)acrylic acid salt as obtained by partial neutralization of (meth)acrylic acid with an alkali metal hydroxide or carbonate, such as sodium hydroxide, potassium hydroxide, sodium carbonate or potassium carbonate, or ammonium hydroxide, or an amine.

The mixing ratio between them, namely the degree of partial neutralization, should be such that 60–99 (preferably 60–90) mole percent of the whole (meth)acrylic acid be neutralized. In other words, the polymerization should be carried out at a (meth)acrylic acid/water-soluble (meth)acrylic acid salt ratio within the range of 40/60 to 1/99 (mole ratio). When the above ratio exceeds 40/60, the absorbency for water and the rate of water absorption decrease and the product disadvantageously assumes an acid odor. When the ratio is below 1/99, the absorbency for water and the rate of water absorption likewise become low. In either case, the product cannot be of practical use.

The carboxyl group-containing polyvinyl alcohol resin is used in an amount of 0.1–25% by weight, preferably 0.1–10% by weight, based on the total weight of (meth)acrylic acid plus (meth)acrylic acid salt. The use at a level below 0.1% is hardly effective in reducing the water-soluble matter content whereas the use at a level above 25% by weight no more produces any significant additional effect in reducing the water-soluble matter content as compared with the use at a level of 25% but rather leads to a decreased absorbency for water.

The polymerization can be conducted by any of the known methods such as the aqueous solution polymerization, emulsion polymerization or reversed-phase emulsion polymerization, and suspension polymerization or reversed-phase suspension polymerization methods but preferably in the manner of reversed-phase suspension polymerization or solution polymerization. Such preferred methods of polymerization are described below in more detail.

In carrying out the reversed-phase suspension polymerization, an aqueous solution containing a carboxyl group-containing polyvinyl alcohol resin, (meth)acrylic acid and a water-soluble (meth)acrylic acid salt and optionally a crosslinking agent such as a polyfunctional vinyl monomer is dispersed in a water-immiscible organic solvent, and the polymerization is performed in the presence of a radical initiator.

In that case, a known dispersion stabilizer or surfactant can be added to the polymerization system for the purpose of stabilizing the polymerization process.

Examples of the water-immiscible organic solvent are alicyclic hydrocarbons such as cyclohexane and cyclopentane, aliphatic hydrocarbons such as npentane, n-hexane, n-heptane and ligroin, and aromatic hydrocarbons such as benzene, toluene and xylene. From the viewpoints of boiling point, melting point, price and commercial availability thereof, n-hexane and cyclohexane are most suited for practical use.

The polymerization is suitably carried out at a temperature of 50°–90° C. for a period of 0.5–5 hours.

After completion of the polymerization, the product particles are collected by filtration, washed and dried in the conventional manner to give the desired, highly absorbent resin.

In carrying out the solution polymerization, water, a carboxyl group-containing polyvinyl alcohol resin, (meth)acrylic acid, a water-soluble (meth)acrylic acid salt and a radical initiator are mixed together homogeneously. Thereafter, the polymerization is allowed to proceed with or without stirring. And the solid matter obtained is comminuted and dried.

In carrying out the stationary polymerization on an industrial scale, the above-mentioned homogeneous mixture is placed in buckets of a bucket conveyor or supplied onto a belt provided with a dam on either edge or into a tube or charged into a vessel having an arbitrarily chosen shape, and the reaction is allowed to proceed at a temperature of about 40°–100° C. for 0.03–5 hours while the mixture is maintained in a state in which no mixing or stirring action is exerted. After progress of the polymerization to a predetermined conversion, the resin which has solidified is cut or ground to a grain size in the order of a pellet size or below and then dried. The above series of operations is preferably conducted in a continuous manner.

As the polymerization initiator to be used in carrying out the above-mentioned polymerization processes, there may be mentioned azonitriles such as azobisisobutyronitrile; alkyl hydroperoxides such as t-butyl hydroperoxide and cumene hydroperoxide; dialkyl peroxides such as di-t-butyl peroxide; acyl peroxides such as acetyl peroxide, lauroyl peroxide, stearoyl peroxide and benzoyl peroxide; peroxy esters such as t-butyl peroxyacetate, t-butyl peroxyisobutylate and t-butyl peroxypivalate; ketone peroxides such as methyl ethyl ketone peroxide and cyclohexanone peroxide; hydrogen peroxide; ammonium persulfate; potassium persulfate or peroxydiphosphate; and cerium salts.

In carrying out the reversed-phase suspension polymerization, it is practical to stabilize the reaction system preferably by addition of a surfactant. As such surfactant, there may be mentioned nonionic or anionic surfactants such as polyoxyethylene alkyl ethers, polyoxyethylene acyl esters, polyoxyethylene sorbitan fatty acid esters, sorbitan fatty acid esters, oxyethylene-oxypropylene block copolymers, sucrose fatty acid esters, higher alcohol sulfuric acid ester salts, alkylbenzenesulfonic acid salts and polyoxyethylene sulfates. These are used either singly or in combination.

Furthermore, a crosslinking agent is used in combination generally on the occasion of polymerization to thereby secure high-level water-absorbing characteristics.

The crosslinking agent is used in an amount of 0.00001–0.1 mole percent, preferably 0.0001–0.01 mole percent, based on the total amount of (meth)acrylic acid plus (meth)acrylic acid salt. Examples of the crosslinking agent are ethylene glycol diacrylate, ethylene glycol dimethacrylate, diethylene glycol dimethacrylate, triethylene glycol diacrylate, triethylene glycol dimethacrylate, trimethylolpropane triacrylate, tripmethylolpropane trimethacrylate, pentaerythritol triacylate, pentaerythritol trimethacrylate, N,N'-methylenebisacrylamide, triallyl isocyanurate, pentaerythritol diacrylate and pentaerythritol dimethacrylate.

In accordance with the invention, water-absorbing resins composed of partially neutralized (meth)acrylic acid polymers, which are well balanced with respect to absorbency for water, rate of water absorption and insolubility in water, can be obtained by carrying out the polymerization in the presence of a carboxyl group-containing polyvinyl alcohol resin as specified herein.

The highly water-absorbing resins obtained in the above manner are of use in various sanitary materials such as disposable diapers, tampons, sanitary cotton, bandages and napkins. They are also useful as agents for separating water in oils, dehydrating agents or desiccants for other purposes, water-retaining agents for plants and soils and carriers for liquid chromatography, among others.

EXAMPLES

The following examples are further illustrative of the method according to the invention.

EXAMPLE 1

A flat-bottomed separable flask was charged with 40 parts by weight of acrylic acid and 20 parts by weight of a 10% (by weight) aqueous solution of a saponified monomethyl maleate-vinyl acetate copolymer (monomethyl maleate content 4 mole percent, degree of saponification 99.5 mole percent). The contents were stirred for mixing.

An aqueous sodium hydroxide solution was added to the above mixture to thereby neutralize 75 mole percent of the acrylic acid. Then the system was purged with nitrogen and, in a nitrogen atmosphere, 0.8 part by weight of a 5% (by weight) aqueous solution of ammonium persulfate was added, immediately followed by stirring.

The stirring was discontinued and the mixture was allowed to stand for stationary polymerization for 2 hours while the inside temeprature was maintained at 80° C. or below.

Upon cooling after the reaction, a copolymer was obtained in a sheet-like form. This was cut to strips (about 2 mm thick), air-dried at 120° C. and further ground to 40–200 mesh. The performance characteristics of the thus-obtained highly absorbent resin are shown below in the table.

COMPARATIVE EXAMPLE 1

The procedure of Example 1 was followed except that the use of the saponified monomethyl maleate-vinyl acetate copolymer was omitted. The performance characteristics of the resin obtained are shown in the table.

COMPARATIVE EXAMPLE 2

The procedure of Example 1 was followed except that polyvinyl alcohol [viscosity of 4% (by weight) aqueous solution 25 cps (20° C.), degree of saponification 99.5 mole percent] was used in lieu of the saponified monomethyl maleate-vinyl acetate copolymer. The performance characteristics of the resin thus obtained are shown in the table.

EXAMPLE 2

A separable flask was charged with 200 parts by weight of cyclohexane and 1.6 parts by weight of sorbitan monostearate. The mixture was stirred at 30° C. to give a homogeneous solution, followed by nitrogen purging.

Separately, 30 parts by weight of acrylic acid was mixed with 15 parts by weight of a 10% (by weight) aqueous solution of the same saponified monomethyl maleate-vinyl acetate copolymer as used in Example 1, and the acrylic acid was partially neutralized to an extent of 75 mole percent with an aqueous solution of sodium hydroxide.

After nitrogen purging, 0.6 part by weight of a 5% (by weight) aqueous solution of ammonium persulfate was added to said neutralized solution and the resultant mixture was added to the above-mentioned cyclohexane solution. Reversed-phase suspension polymerization was then performed with stirring at 70° C. (inside temperature) for 3 hours.

After completion of the reaction, the system was cooled to 30° C., the contents were filtered through a 300-mesh wire netting, and the polymer on the filter was washed thoroughly with cyclohexane. After drying in a hot-air drying chamber at 120° C. for 2 hours, the polymer was ground to 100–350 mesh. Thus was obtained a highly absorbent resin.

The performance characteristics of this resin are shown in the table.

EXAMPLES 3–9

The procedure of Example 1 or Example 2 was followed except that the conditions employed were as shown in the table. The results thus obtained are shown in the table.

The physical properties were evaluated by the following methods:

(1) Absorbency for deionized water

A 0.1-g portion of a sample was allowed to stand in 150 ml of deionized water for 1 hour. The mixture was filtered using a 325-mesh wire netting, and the filtrate water was weighed (A grams).

The absorbency was expressed in terms of the ratio:

$$\frac{150 - A}{0.1}$$

(2) Absrobency for aqueous sodium chloride solution

A 0.2-g portion of a sample was allowed to stand in 60 ml of a 0.9% (by weight) aqueous solution of sodium chloride for 20 minutes, the mixture was then filtered through a 325-mesh wire netting, and the filtrate water was weighed (B grams).

The absorbency was expressed in terms of the ratio:

$$\frac{60 - B}{0.2}$$

(3) Soluble matter

The percentage soluble matter was calculated as follows:

$$\frac{\text{Residue on evaporation of filtrate } A \text{ (grams)}}{0.1} \times 100 \, (\%)$$

(4) Rate of water absorption

A 0.1-g portion of a sample was placed in a glass bottle having a diameter of 40 mm, 20 g of purified water was then added, and the time (in seconds) required for the contents to stop moving even when the bottle was turned upside down was measured.

|  | Saponified unsaturated carboxylic acid-vinyl acetate copolymer | | | |
|---|---|---|---|---|
|  | Acid | Degree of modification (mole %) | Degree of saponification (mole %) | Amount (% by weight relative to monomer) | Mode of polymerization |
| Example | | | | | |
| 1 | Monomethyl maleate | 4 | 99.5 | 5.0 | Stationary |
| 2 | Monomethyl maleate | 4 | 99.5 | 5.0 | Reversed-phase suspension |
| 3 | Monomethyl maleate | 4 | 99.5 | 1.0 | Reversed-phase suspension |
| 4 | Monomethyl maleate | 4 | 90.0 | 10.0 | Reversed-phase suspension |
| 5 | Monomethyl maleate | 2 | 99.5 | 1.0 | Reversed-phase suspension |
| 6 | Monomethyl maleate | 10 | 99.5 | 10.0 | Reversed-phase suspension |
| 7 | Itaconic acid | 4 | 85.0 | 5.0 | Reversed-phase suspension |
| 8 | Itaconic acid | 4 | 99.5 | 5.0 | Stationary |
| 9 | Acrylic acid | 2 | 99.5 | 1.0 | Reversed-phase suspension |
| Comparative Example | | | | | |
| 1 | — | — | — | — | Stationary |
| 2 | — |  | 0 | 99.5 | 1.0 | Stationary |

| Resin performance characteristics | | | |
|---|---|---|---|
| Absorbency for deionized water (volumes) | Absorbency for aqueous sodium chloride solution (volume) | Soluble matter (% by weight) | Rate of water absorption (seconds) |
| 800 | 80 | 8 | 34 |
| 820 | 83 | 7 | 34 |
| 710 | 76 | 8.5 | 35 |
| 800 | 80 | 7 | 34 |
| 780 | 80 | 9 | 35 |
| 720 | 82 | 9 | 34 |
| 800 | 82 | 8 | 35 |
| 780 | 80 | 8 | 35 |
| 760 | 78 | 9 | 35 |
| 610 | 70 | 15 | 50 |
| 660 | 70 | 13 | 45 |

What is claimed is:

1. A method of producing highly water-absorbing resins which comprises polymerizing acrylic or methacrylic acid respectively together with a water-soluble acrylic or methacrylic acid salt in the presence of a carboxyl group-containing polyvinyl alcohol resin consisting of saponified vinyl ester-ethylenically unsaturated carboxylic acid copolymer wherein the carboxyl group content of the carboxyl group-containing polyvinyl alcohol resin is in the range of 0.1–30 mole percent.

2. The method of claim 1, wherein the mole ratio between the acrylic or methacrylic acid and the water-soluble acrylic or methacrylic acid salt is 40:60 to 1:99.

3. The method of claim 1, wherein the mole ratio between the acrylic or methacrylic acid and the water-soluble acrylic or methacrylic acid salt is 40:60 to 10:90.

4. The method of claim 1, wherein the carboxyl group-containing polyvinyl alcohol resin is used in an amount of 0.1–25% by weight based on the total amount of acrylic or methacrylic acid plus water-soluble acrylic or methacrylic acid salt.

5. The method of claim 1, wherein the carboxyl group-containing polyvinyl alcohol resin is used in an amount of 0.1–10% by weight based on the total amount of acrylic or methacrylic acid plus water-soluble acrylic or methacrylic acid salt.

6. The method of claim 1, wherein the carboxyl group content in the carboxyl group-containing polyvinyl alcohol resin is 0.5–10 mole percent.

7. The method of claim 1, wherein the ethylenically unsaturated carboxylic acid is monomethyl maleate.

8. The method of claim 1, wherein the water-soluble acrylic or methacrylic acid salt is the sodium salt.

9. The method of claim 1, wherein the polymerization is caried out in the manner of stationary polymerization.

10. The method of claim 1, wherein the polymerization is carried out in the manner of reversed-phase suspension polymerization.

* * * * *